United States Patent [19]

Hirata

[11] Patent Number: 4,602,501

[45] Date of Patent: Jul. 29, 1986

[54] RHEOMETER

[76] Inventor: Keisuke Hirata, 1920-1, Noginomori-cho, 4-chome, Ogaki-shi, Gifu-ken 503, Japan

[21] Appl. No.: 700,708

[22] PCT Filed: May 14, 1984

[86] PCT No.: PCT/JP84/00241

§ 371 Date: Jan. 30, 1985

§ 102(e) Date: Jan. 30, 1985

[87] PCT Pub. No.: WO84/04812

PCT Pub. Date: Dec. 6, 1984

[30] Foreign Application Priority Data

May 31, 1983 [JP] Japan .................................. 58-96700
Feb. 25, 1984 [JP] Japan .................................. 59-34838

[51] Int. Cl.$^4$ ........................................... G01N 11/10
[52] U.S. Cl. ....................................................... 73/54
[58] Field of Search ..................................... 73/54, 57

[56] References Cited

U.S. PATENT DOCUMENTS 2,957,338 10/1960 Kennedy et al. ........................ 73/54
3,967,934 7/1976 Seitz et al. ........................... 73/57 X

FOREIGN PATENT DOCUMENTS 51-131385 4/1976 Japan .
55-26766 3/1980 Japan .
842486 7/1981 U.S.S.R. .................................. 73/54
1081474 3/1984 U.S.S.R. .................................. 73/54

OTHER PUBLICATIONS

Low-Shear 30 catalog, Contraves, Switzerland.
Rotovisco RV 100, CV 100 catalog, Haake, West Germany.
Oscillating Plate Viscometer by Oka, S, 1960, Academic Press, NY, pp. 65-67.
Parallel Plate Plastomer by Oka, S, 1960, Academic Press, NY, pp. 73-75.
Rheology of Biological Systems, Lutz, R. J. et al., 1973, pp. 130-139.
Rheological Properties of Microliter Quantities of Normal Mucus, King, M. et al., pp. 797-802.
A Modified Oscillating Sphere Magnetic Microrheometer For Use With Biological Secretions, James, S. L. et al, 1982, pp. 179-180.

*Primary Examiner*—Stewart J. Levy
*Assistant Examiner*—Joseph W. Roskos
*Attorney, Agent, or Firm*—Birch, Stewart, Kolasch & Birch

[57] ABSTRACT

A movable-piece type of rheometer having a sensing member that can measure a fluid or viscoelastic material which moves relative to the sensing member, by a control of the sensing member to a position or movement desired in a non-contact manner. The rheometer uses magnetic force through a servomechanism instead of a mechanical support structure. This rheometer is useful in fields such as biorheological and rheological studies, and rheological examination, usage and production.

16 Claims, 2 Drawing Figures

RHEOMETER

DESCRIPTION

1. Related Technical Field

The invention relates to a viscometer, an elastometer, a viscoelastometer or a rheometer. Hereafter they all are called rheometer as a general term. In a movable-piece type of rheometer, a part of the movable-piece or the whole of the piece is immersed in or contacting with or fixed to a viscoelastic sample to be measured, and it makes relative motion as a sensing member to the sample. Force on the movable-piece is influenced by the rheological properties of the sample. The rheological properties of the sample are determined usually according to the relation between the force on the sensing member and the relative motion of the sensing member to the measured sample.

2. Background Art

The drive or support mechanism in the prior art systems involves elastic supporting elements, for example, torsion bars or plate springs, or bearing elements, for example, rotary bearings or linear sliding bearings.

In some types of conventional movable-piece rheometer a movable-piece is plunged into the gel-like high viscoelastic sample.

But such a mechanical support structure as an elastic support structure or a bearing has complicated structure and is easily damaged. It is inconvenient to change samples. Moreover they have difficulty in measuring a small amount of sample because it is impossible to manufacture a very small dimension of movable-piece and it is difficult to measure at high test frequencies. The movable-piece which is plunged into a sample is difficult in holding itself in the intended sensing position because of its gradual dislocation during measurement.

DISCLOSURE OF THE INVENTION

The present invention solves these serious problems in the conventional rheometers as mentioned above, and provides a rheometer and a convenient method to determine precisely the rheological properties of a sample with a very small amount of the sample covering high test frequency with simple mechanical structure.

That is, a rheometer of the present invention is characterized in that, when it determines viscosity, elasticity or rheological properties of a sample material from the relative motion of a sensing member to the sample, a magnetic movable-piece as a sensing member immersed in, contacting with or fixed to a sample material by a magnetic drive or support means for controlling the relative position or motion of said movable-piece to the sample material by magnetic force through a servo-mechanism following predetermined position or motion in a non-contact manner instead of any mechanical drive or support structure.

The present invention has merits and advantages mentioned below.

(a) A rheometer of the present invention has no mechanical support structure. Therefore, a very small sensing-member can be manufactured. It does not require troublesome adjustment of the support structure. No deformation or destruction of the support structure is encountered in changing samples. It provides long mechanical life without any trouble around support structure. A movable-piece and a sample can be sealed hermetically in a disposable container cartridge. So that, the same container for storage can be used also for measurement, and it provides quick convenient change of samples without contamination of samples, repetition of measurement of the same sample, and it avoids denaturalization due to evaporation, scattering of, for example, radioactive samples. Temperature control, for example, warming or cooling of a sample material is managed easily.

(b) A very small sensing-member can be employed. Therefore, the rheometer can measure accurately a very small amount of sample. The sensing-member accurately works even at high test frequency, and it is hardly interrupted by mass effect of a movable-piece.

(c) The movable-piece does not touch a container wall, and is not influenced by support structure. Therefore, the rheometer accurately measures even low viscoelastic samples and even in test condition of very small viscoelastic force. Calibration of the magnetic force against the coil current is easily performed using the gravitational accelleration, and it yields good accuracy and good reproducibility of measurement.

(d) The sensitivity of the instrument is easily regulated by changing the characteristics of the servomechanism, and the measurement covers a wide viscoelastic range from low values to high and a wide frequency range.

(DESIGNATION NUMBERS AND ELEMENTS)

Figure 1:
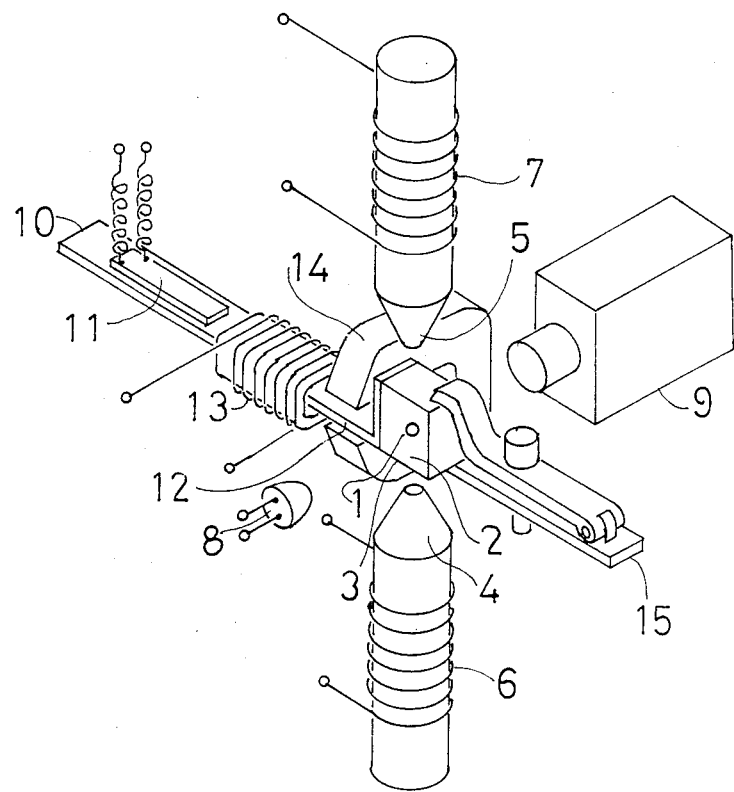
FIG. 1 is a perspective schematic representation of the main portions of one preferred embodiment of the present invention.

1: movable-piece (sensing member)
2: sample material
3: sample container
4,5: magnet core
6,7: magnet coil
8: light source
9: displacement measuring device
10: bracket
11: displacement measuring device
12: magnetic plate
13: vibrator coil
14: field magnet
15: container clump
16,17: D.C. power amplifier
18: wave generator
19: operational amplifier
20: compensation circuit
21,22: resistor

BEST MODE FOR CARRYING OUT THE INVENTION

Referring to the attached drawings, the details of the present invention is described below.

FIG. 1 is a perspective schematic representation of the main portions of one embodiment of the present invention. A movable-piece 1 as a sensing member is a sphere fully or partly composed of magnetic material, for example, soft iron, and is immersed in a viscoelastic sample material 2 sealed hermetically in a sample container 3 with transparent windows. Magnet cores 4,5 which are wound with magnet coils 6,7 of, for example, enameled copper wires composes a pair of electromagnets facing each other. A displacement measuring device 9, for example, a non-contact optoelectronic tracker detects the displacement of the image of the movable-piece 1 transmitted by a light beam from a light source 8, for example, an electric lamp. The sample container 3 is fixed to the free end of a bracket 10. The bracket 10 is a cantilever of an elastic substance, for example, phosphor bronze, and is equipped with a displacement measuring device 11, for example, an electric resistance wire strain gauge which detects the displacement of the sample container 3. A magnetic plate 12 is fixed near the free end of the bracket 10, and the sample container 3 vibrates vertically in the co-axial direction between the pair of magnet cores 4,5. A container clamp 15 is used in moving probe mode when only the movable-piece is reciprocated but the container 3 is fixed.

Figure 2:
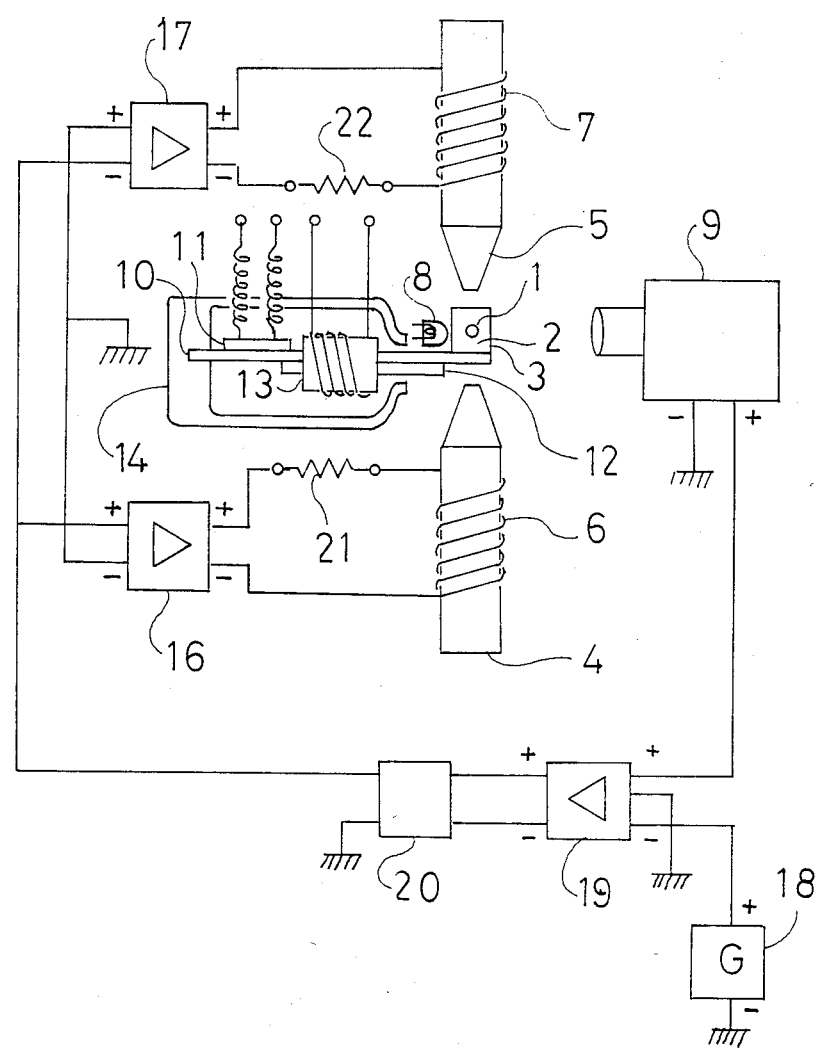
FIG. 2 is a diagram of the electric circuit of one preferred embodiment of the present invention.

FIG. 2 is a diagram of the electric circuit of one embodiment of the present invention. Driving currents are supplied to the magnet coils 6,7 by D.C. power amplifiers 16,17. Resistors 21,22 detect coil currents of the magnet coils 6,7 respectively.

In order to hold the movable-piece 1 in the same position or to put it in intended motion, the servomechanism of a preferred embodiment of the present invention consists as follows. A displacement measuring device 9 produces a signal voltage proportional to the displacement of said movable-piece 1. A signal voltage which indicates position or motion to be followed is introduced by a wave generator 18. An operational amplifier 19 produces a signal voltage indicating the dislocation of the movable-piece 1 at the instance a reference standard signal voltage indicates an intended position, and produces a differential signal voltage, which is fed into D.C. power amplifiers 16,17, and they supply drive currents to the magnet coils 7,8, and reduce deviation of the movable-piece 1 from the intended position. A compensation circuit 20 consists of, for example, P(proportional), I(integral), D(differential) circuits and provides quick response and good stability of the servo-system.

As for measurement of the displacement of the movable-piece 1 or the sample container 3, any type of means for non-contact displacement measurement can be employed. Beside the optoelectronic tracker used in said embodiment, other devices can be used such as conventional devices for displacement measurement employing photoelectric principles, for example a photocell and a photodiode, conventional devices using radiant rays, electromagnetic waves, for example, using X-rays or gamma-rays and ultrasonic waves.

For sensing of the position of the sample container 3, comparatively bulky methods in a contact manner can be also applied. They are an electromagnetic device, for example, a pick-up coil or a differential transformer, an electrocapacitance device and an electric resistance wire strain gauge.

It is possible at various points in the servo-system to input the signal of the relative displacement or motion between the movable-piece 1 and the sample container 3. Usually it is convenient to set the position or displacement directly by a reference standard voltage to an operational amplifier 19 by a wave generator 18. Another method is carried out by inputting to a servo-system a direct current component, which indicates an average position of the movable-piece 1. And an oscillatory component is fed to the system outside the servomechanism. Other methods are performed by setting the displacement of a light source 8, a displacement measuring device 9 or a sample container 3.

In high frequency oscillation, alternation of the coil current, that is, of the magnetic force lags in phase behind a supplied voltage across the magnet coils 6,7 due to a coil inductance. Therfore, basically the direct control of the coil currents is preferable from the viewpoint of characteristics of a servomechanism.

As for the shape of the movable-piece 1, a sphere is preferable, because it is symmetrical in every direction, mechanically strong, easy to be manufactured and convenient to analyse as a theoretical model. However, parallel motion of a needle, a strip or a plate, or rotational motion of a column, a cylinder, a cone or a disc may be also appliable. In order to establish and control rotational motion of a disc-shaped movable-piece by magnetic force, a moment is produced by magnetic drive unit with its magnetic poles placed in a tangential direction on a magnetic tip to the rim of the disc-shaped movable-piece. Another method is a circular arrangement of electric field magnets around the movable-piece 1, which generates rotational magnetic field and produces a moment by an induction effect. Those are well known conventional methods used in electric rotary machines. Detection of the position or motion of a movable-piece is also capable at the same point where the magnetic force works. In this case, if preferred, supplementary supporting elements, for example rotary bearings such as a magnetic bearing, a fluid bearing or a mechanical bearing may be additionary used. Of course the elements do not spoil the advantages of the invention because they do not disturb or restrict intended relative motion.

As for solid viscoelastic material, the movable-piece 1 may be attached to the sample material 2. In the influence of magnetic field by magnetic drive unit the movable-piece 1 gives external force on the sample material 1 and produces tension, compression, bending, shearing or torsion in the material. And the relation between the external force and the deformation of the sample yields rheological properties of the sample.

The working mechanism of one embodiment of the invention is described hereafter. Suppose, for example, the polarity is chosen so that the output signal voltage becomes positive when the movable-piece 1 makes displacement upward relative to a standard point in the view screen of the displacement measuring device 9. In order to input a signal which indicates intended position of the movable-piece 1, a signal generator 18 may be so adjusted as to produce the same signal voltage as the output voltage from a displacement measuring device 9 to be expected.

In measuring by a method of holding a movable-piece 1 stationary in a fixed position, referring to FIG. 2, if the movable-piece 1 locates above the intended position indicated by a wave generator 18, the output from the operational amplifier 19 will becomes positive, and driving current through the magnet coil 6 from the D.C. power amplifier 16 will increase, on the other hand driving current through magnet coil 7 from a D.C. power amplifier 17 will decrease consequently resulting that the movable-piece 1 will be tracted downward by magnetic force. To the contrary, if the movable-piece 1 locates below the intended position, it will be tracted upward by magnetic force. When the movable-piece 1 arrives the intended position the output signal voltage from the operational amplifier 19 becomes naught and the magnetic force which tracts the movable-piece 1 is not produced.

If it is desired that the movable-piece 1 moves following an intended motion, all necessary is only that a signal voltage from a wave generator 18 varies in the same pattern as an intended motion. To perform measurement, the embodiment of the invention can be used in either of the two measuring modes, which are a moving container mode and a moving probe mode, by selecting among them. In a moving container mode, the movable-piece 1 is held stationary at the fixed position and a vibrator coil 13 moves the sample container 3. Instead, in a moving probe mode, the sample container 3 is held stationary by a container clamp 15 and a movable-piece 1 moves according to the signal from a wave generator 18.

The viscoelastic values of a sample material 2 is determined according to the magnetic force on a movable-piece 1 and relative motion between the movable-piece 1 and the sample material 2. Although the magnetic force can be estimated using voltage drop across resistors 21, 22 for a measure of coil currents, but practically it is convenient to perform calibration of the magnetic force by either of the gravitational accelleration on the movable-piece 1 or sinusoidal oscillation of the movable-piece 1 in a Newtonian fluid of known viscosity using the same values for the driving currents.

A relative displacement between a movable-piece 1 and a sample material 2 is measured in a moving container mode according to the displacement of the sample container 3, and in a moving probe mode according to the motion of the movable-piece 1, that is, according to an output signal voltage from the displacement measuring device 9 respectively.

Calculation of the viscoelasticity is performed as follows. Firstly described is the calibration of magnetic force against a coil current by standard of the gravitational accelleration. Suppose that the co-axis between the magnet cores 4 and 5 are arranged exactly in the perpendicular direction. In unloaded condition, that is, when the differential signal voltage from an operational amplifier 19 is switched off to naught, the drive currents 6,7 becomes the same value $i_0$. After then, by adjusting the reference standard voltage from a wave generator 18 so that the movable-piece 1 may be suspended exactly in the center of the gap between the magnet cores 4,5, $$i_1 = i_0 - i_G$$

$$i_2 = i_0 + i_G$$

when the amplitude of the current oscillation is small, the change of magnetic force may be assumed to be proportional to the change of the coil current, $$i_G \alpha (4/3)\pi r^3 (\rho_s - \rho_f) g$$

when the test frequency is not so high, $$F = (4/3)\pi r^3 (\rho_s - \rho_f) g (i_n - i_2)/i_G$$

$$i_G = i_2 - i_0$$

where
$i_0$: current through coil 6 without any load
$i_1$: current through coil 6 with gravitational load
$i_2$: current through coil 7 with gravitational load
$i_G$: current shift by gravitational load
$i_n$: current through coil 7 in measurement
r: radius of a sphere
$\rho_s$: density of a sphere
$\rho_f$: density of a sample material
g: gravitational accelleration
F: magnetic force Complex modulus and viscosity is calculated, for example, using a sphere as a movable-piece 1 and simple oscillation displacement to a viscoelastic material. When recording the relation between the force on a movable-piece 1 and relative motion, for example, the magnetic force is plotted in horizontal axis and the displacement of the movable-piece 1 is plotted vertical axis on an oscilloscope. The magnetic force is measured by current through resistor 22, and the displacement is measured by the displacement measuring device 9 and the Lissadius-loop of them on an oscilloscope results in an ellipse. The phase lag of displacement to magnetic force is determined according to the shape of the ellipse.

sin $\alpha$ = (major axis * minor axis of ellipse)/(area of rectangle whose side is parallel to the horizontal axis, circumscribed to ellipse)

Complex modulus is defined by $$G^* = G' + iG''$$
$$= \overline{G}(\cos\delta + i\sin\delta)$$

Applying Stokes' law approximately to the viscous drag on a sphere, $$F = G^* 6\pi r X e^{i(\omega t - \delta)}$$

and $$\overline{G} = \overline{F}/6\pi r \overline{X}$$

so that, $$\overline{G'} = G \cos \delta$$

$$\overline{G''} = G \sin \delta$$

$$\eta = G''/\omega$$

where
$G^*$: complex modulus (complex elasticity)
$G'$: storage modulus (dynamic elasticity)
$G''$: loss modulus
$\overline{G}$: absolute value of complex modulus
$\overline{F}$: amplitude of magnetic force oscillation
$\overline{X}$: amplitude of displacement oscillation
$\eta$: viscosity
e: base of natural logarithm
i: imaginary unit
$\omega$: angular frequency
$\delta$: phase lag
t: time

CAPABILITY OF INDUSTRIAL USE

The present invention is valuable as an apparatus for rheological measurement and its simple mechanical structure provides easy manufacture of it and convenient operation. It is useful in such fields as rheological, especially biorheological studies where only a very small amount of sample is available, and in such fields as examination, usage and production of rheological material, because of convenient operation and quick measurement.

I claim:

1. A rheometer for measuring viscoelasticity of a sample material comprising:
   a sample container for holding said material,
   means for positioning said container,
   a magnetic movable-piece located in said material to serve as a sensing member,
   at least one electromagnet placed adjacent said movable-piece,
   means for detecting the displacement of said movable-piece,
   an electronic servomechanism means for adjusting the displacement of said movable-piece in a noncontact manner following a predetermined displacement by controlling the excitation currents of said at least one electromagnet, and
   means for introducing a signal into said servomechanism which indicates the predetermined displacement.

2. A rheometer, as claimed in claim 1, wherein said electronic servomechanism means includes an optical displacement detector for measurement of the displacement of said sample container.

3. A rheometer, as claimed in claim 1, wherein said electronic servomechanism means includes a radiant ray displacement detector for measurement of the displacement of said sample container.

4. A rheometer, as claimed in claim 1, wherein said electronic servomechanism means includes an ultrasonic displacement detector for measurement of the displacement of said sample container.

5. A rheometer, as claimed in claim 1, wherein said electronic servomechanism includes an electromagnetic displacement detector for measurement of the relative displacement of said sample container.

6. A rheometer, as claimed in claim 1, wherein said electronic servomechanism includes an electroresistance strain gauge for measurement of the relative displacement of said sample container.

7. A rheometer, as claimed in claim 1, wherein said means for introducing a signal includes apparatus for setting a standard reference voltage of the servomechanism.

8. A rheometer, as claimed in claim 1, wherein said means for introducing a signal include apparatus for setting a direct current component which indicates average position of said movable-piece.

9. A rheometer, as claimed in claim 1, wherein said means for introducing a signal includes apparatus responsive to motion of a displacement detecting device.

10. A rheometer, as claimed in claim 1, wherein said means for introducing a signal includes apparatus responsive to motion of said sample container.

11. A rheometer, as claimed in claim 1, wherein said movable-piece is shaped as a sphere.

12. A rheometer, as claimed in claim 1, wherein said movable-piece is shaped as a column.

13. A rheometer, as claimed in claim 1, wherein said movable-piece is shaped as a cone.

14. A rheometer, as claimed in claim 1, wherein said movable-piece is shaped as a disc.

15. A rheometer, as claimed in claim 1, wherein said movable-piece is shaped as a needle.

16. A rheometer, as claimed in claim 1, wherein said magnetic movable-piece is fixed to said sample material.

* * * * *